US012338816B2

(12) United States Patent
Govari

(10) Patent No.: US 12,338,816 B2
(45) Date of Patent: Jun. 24, 2025

(54) PROGRESSIVE CAVITY PUMP CARTRIDGE WITH INFRARED TEMPERATURE SENSORS ON FLUID INLET AND OUTLET

(71) Applicant: JOHNSON & JOHNSON SURGICAL VISION, INC., Irvine, CA (US)

(72) Inventor: Assaf Govari, Haifa (IL)

(73) Assignee: Johnson & Johnson Surgical Vision, Inc., Irvine, CA (US)

(*) Notice: Subject to any disclaimer, the term of this patent is extended or adjusted under 35 U.S.C. 154(b) by 185 days.

(21) Appl. No.: 17/385,740

(22) Filed: Jul. 26, 2021

(65) Prior Publication Data

US 2023/0028279 A1    Jan. 26, 2023

(51) Int. Cl.
  *F04C 14/06*    (2006.01)
  *F04C 14/28*    (2006.01)

(52) U.S. Cl.
  CPC .............. *F04C 14/06* (2013.01); *F04C 14/28* (2013.01); *F04C 2270/22* (2013.01)

(58) Field of Classification Search
  CPC ...... F04C 14/28; F04C 2270/22; F04C 14/06; F04C 2240/81; F04C 2270/19; F04C 2/1071; A61F 9/00736; A61M 2205/3368; A61M 2210/0612; A61M 1/72; A61M 1/73; A61M 1/77; A61M 1/80; A61M 1/71; A61M 1/74; A61M 3/0216; A61M 1/00; A61M 1/743; A61M 1/774; A61M 2205/0216; A61M 2205/3306; A61M 2205/3331; A61M 2205/3337; A61M 3/0201; A61M 3/0258; A61M 5/14228; F05D 2270/3032; F04D 3/02; F04D 15/0088; F04D 15/0263; F04B 49/10; A61B 2017/00084; A61B 2217/005; A61B 2217/007

(Continued)

(56) References Cited

U.S. PATENT DOCUMENTS

| 4,823,552 A | * | 4/1989 | Ezell ..................... F04B 49/065 60/449 |
| 6,312,226 B1 | * | 11/2001 | Senior, Jr. ............... F04D 13/10 417/63 |

(Continued)

FOREIGN PATENT DOCUMENTS

GB    2253245 A    9/1992

OTHER PUBLICATIONS

Using Thermal Imaging to Monitor Motors and Gearboxes, Fluke Corporation, May 1, 2020.

(Continued)

*Primary Examiner* — Charles G Freay
*Assistant Examiner* — Benjamin Doyle

(57) ABSTRACT

A system includes a pump, an inlet sensor, an outlet sensor, and a controller. The pump is configured for pumping fluid in a phacoemulsification system. The inlet sensor is coupled with an inlet port of the pump and is configured to sense an inlet temperature of the fluid at the inlet port. The outlet sensor is coupled with an outlet port of the pump and is configured to sense an outlet temperature of the fluid at the outlet port. The controller is configured to take a responsive action based a difference between the inlet temperature and the outlet temperature crossing a defined threshold.

15 Claims, 3 Drawing Sheets

(58) Field of Classification Search
USPC .......................................................... 417/32
See application file for complete search history.

(56) References Cited

U.S. PATENT DOCUMENTS

| | | | |
|---|---|---|---|
| 9,509,923 B2 | 11/2016 | Pandey et al. | |
| 11,033,728 B2* | 6/2021 | Schenck | A61M 60/148 |
| 2002/0019607 A1* | 2/2002 | Bui | A61F 9/00745 |
| | | | 604/67 |
| 2003/0036682 A1* | 2/2003 | Leber | A61M 1/77 |
| | | | 604/93.01 |
| 2004/0204679 A1* | 10/2004 | Visconti | A61M 3/0201 |
| | | | 604/131 |
| 2005/0281683 A1* | 12/2005 | Brown | F04D 29/181 |
| | | | 417/313 |
| 2006/0222533 A1* | 10/2006 | Reeves | A61M 60/531 |
| | | | 417/423.1 |
| 2008/0146679 A1* | 6/2008 | Archambeau | B01F 23/233 |
| | | | 351/159.68 |
| 2008/0234619 A1* | 9/2008 | Fausset | A61F 7/12 |
| | | | 604/4.01 |
| 2009/0008306 A1* | 1/2009 | Cicchello | A61M 1/1688 |
| | | | 210/103 |
| 2009/0068024 A1* | 3/2009 | Amburgey | F04C 13/008 |
| | | | 417/253 |
| 2009/0317261 A1* | 12/2009 | Bruce | F04D 15/0263 |
| | | | 417/32 |
| 2010/0228223 A1* | 9/2010 | Williams | A61M 5/142 |
| | | | 604/113 |
| 2011/0137231 A1* | 6/2011 | Sorensen | A61F 9/00745 |
| | | | 604/22 |
| 2012/0065580 A1* | 3/2012 | Gerg | A61M 1/74 |
| | | | 604/28 |
| 2012/0106016 A1* | 5/2012 | Fausset | A61M 5/142 |
| | | | 361/104 |
| 2012/0138272 A1* | 6/2012 | Zimmerman | F04B 15/06 |
| | | | 417/32 |
| 2012/0171049 A1* | 7/2012 | Paluncic | F16N 13/00 |
| | | | 417/32 |
| 2013/0099931 A1* | 4/2013 | Wetherill | G01F 1/34 |
| | | | 340/606 |
| 2014/0163455 A1* | 6/2014 | Wilson | A61M 1/774 |
| | | | 604/28 |
| 2014/0250580 A1* | 9/2014 | Magyar | F04D 15/0088 |
| | | | 417/63 |
| 2014/0334945 A1* | 11/2014 | Koehl | G05B 15/02 |
| | | | 417/44.11 |
| 2016/0279321 A1* | 9/2016 | Bansal | A61M 3/0202 |
| 2017/0189231 A1* | 7/2017 | Baxter | A61M 1/77 |
| 2017/0216093 A1* | 8/2017 | Kuebler | A61M 3/0216 |
| 2017/0241414 A1* | 8/2017 | Billing | F04B 49/10 |
| 2017/0266036 A1* | 9/2017 | Taylor | A61F 7/0053 |
| 2018/0017623 A1 | 1/2018 | Zillinger et al. | |
| 2018/0056024 A1* | 3/2018 | Harrington | A61M 16/161 |
| 2018/0243491 A1* | 8/2018 | Wiesener | A61M 60/422 |
| 2018/0280191 A1* | 10/2018 | Taylor | A61F 7/0053 |
| 2018/0318131 A1* | 11/2018 | Boukhny | A61M 3/0233 |
| 2019/0162063 A1* | 5/2019 | Brown | F04D 13/10 |
| 2019/0351118 A1* | 11/2019 | Graichen | A61M 60/554 |
| 2019/0390538 A1* | 12/2019 | Frantz, III | E21B 33/12 |
| 2020/0164116 A1* | 5/2020 | Gordon | A61M 1/74 |
| 2021/0143493 A1* | 5/2021 | Hoffmann | B60L 1/003 |
| 2021/0205507 A1* | 7/2021 | Heeren | A61M 3/0212 |
| 2021/0379257 A1* | 12/2021 | Pouchoulin | G05D 23/1917 |
| 2022/0143299 A1* | 5/2022 | Sutter | A61M 1/77 |
| 2022/0330958 A1* | 10/2022 | Mobley | A61M 1/64 |
| 2022/0331512 A1* | 10/2022 | Baxter | A61M 1/743 |
| 2024/0131899 A1* | 4/2024 | Malone | H01M 10/613 |

OTHER PUBLICATIONS

Narayanan, Shankar Bhaskaran. Fluid Dynamic and Performance Behavior of Multiphase Progressive Cavity Pumps. Diss. Texas A & M University, 2012.

Thermal monitoring with infrared sensors (https://www.processingmagazine.com/process-control-automation/instrumentation/article/15587285/thermal-monitoring-with-infrared-sensors).

U.S. Appl. No. 17/318,665, filed May 12, 2021 and titled "Disposable Pump Cartridge".

Plant Engineering—Understanding progressive cavity pumps (https://www.plantengineering.com/articles/understanding-progressive-cavity-pumps/) Oct. 1, 2000.

Seepex, Operating and Maintenance Instructions—Progressive Cavity Pump. Oct. 12, 1994.

* cited by examiner

PROGRESSIVE CAVITY PUMP CARTRIDGE WITH INFRARED TEMPERATURE SENSORS ON FLUID INLET AND OUTLET

FIELD OF THE INVENTION

The present invention is related generally to the eye surgery, and particularly to phacoemulsification pumps.

BACKGROUND OF THE INVENTION

Techniques for monitoring temperature of a pump have been previously proposed in the patent literature. For example, U.S. Patent Application Publication 2014/0250580 describes a pump system including a motor, a fluid pump powered by the motor, a temperature sensor, and a controller. The controller including a processor and a computer readable memory storing instructions that, when executed by the processor, cause the controller to receive a first temperature value from the temperature sensor, receive a second temperature value from the temperature sensor, calculate a rate of temperature change by comparing the first temperature value and the second temperature value, calculate a heating offset value based on the rate of temperature change, and calculate an ambient temperature based on the second temperature value and the heating offset value.

As another example, U.S. Pat. No. 6,312,226 describes a device and method for detecting bearing overheating in oil-lubricated turbine pumps comprising a temperature transmitting collar and infrared sensor. The temperature transmitting collar is mounted on the pump line shaft immediately adjacent to the stretch bearing, which is the top bearing in the pump system. The infrared sensor is positioned within sensing distance of the temperature transmitting collar and control circuitry is provided to warn of abnormal temperatures and to turn the pump off if temperatures continue to rise to an alarm condition.

SUMMARY OF THE INVENTION

An embodiment of the present invention that is described hereinafter provides a system including a pump, an inlet sensor, an outlet sensor, and a controller. The pump is configured for pumping fluid in a phacoemulsification system. The inlet sensor is coupled with an inlet port of the pump and is configured to sense an inlet temperature of the fluid at the inlet port. The outlet sensor is coupled with an outlet port of the pump and is configured to sense an outlet temperature of the fluid at the outlet port. The controller is configured to take a responsive action based on a difference between the inlet temperature and the outlet temperature crossing a defined threshold.

In some embodiments, the controller is configured to detect a too high temperature of the pump by detecting a too high temperature difference between the inlet temperature and the outlet temperature.

In some embodiments, the controller is configured to compare a difference between the outlet temperature and the inlet temperature to a threshold, and to take the responsive action when the difference exceeds the threshold.

In an embodiment, the controller is configured to estimate an absolute temperature of the pump based on the readings of the inlet sensor and the outlet sensor, and to take the responsive action upon detecting the too high absolute temperature.

In an embodiment, the responsive action includes shutting down the pump.

In some embodiments, the inlet sensor and the outlet sensor are infrared sensors.

In some embodiments, the pump is a progressive cavity pump.

In an embodiment, the pump is one of an irrigation pump and an aspiration pump.

In another embodiment, the pump, the inlet sensor and the outlet sensor are part of a removably insertable cartridge for use in the phacoemulsification system.

In some embodiments, the controller comprises a processing circuitry which is configured to detect a temperature of the pump based on readings of the inlet sensor and the outlet sensor, and take a responsive action based on the temperature.

There is additionally provided, in accordance with another embodiment of the present invention, a method including sensing an inlet temperature of a fluid at an inlet port of a pump for pumping fluid in a phacoemulsification system and sensing an outlet temperature of the fluid at a respective outlet port of the pump. A temperature of the pump is detected based on readings of the inlet and the outlet fluid temperatures, and a responsive action is taken based on a difference between the inlet temperature and the outlet temperature crossing a defined threshold.

The present invention will be more fully understood from the following detailed description of the embodiments thereof, taken together with the drawings in which:

DETAILED DESCRIPTION OF EMBODIMENTS

Overview

Figure 1:
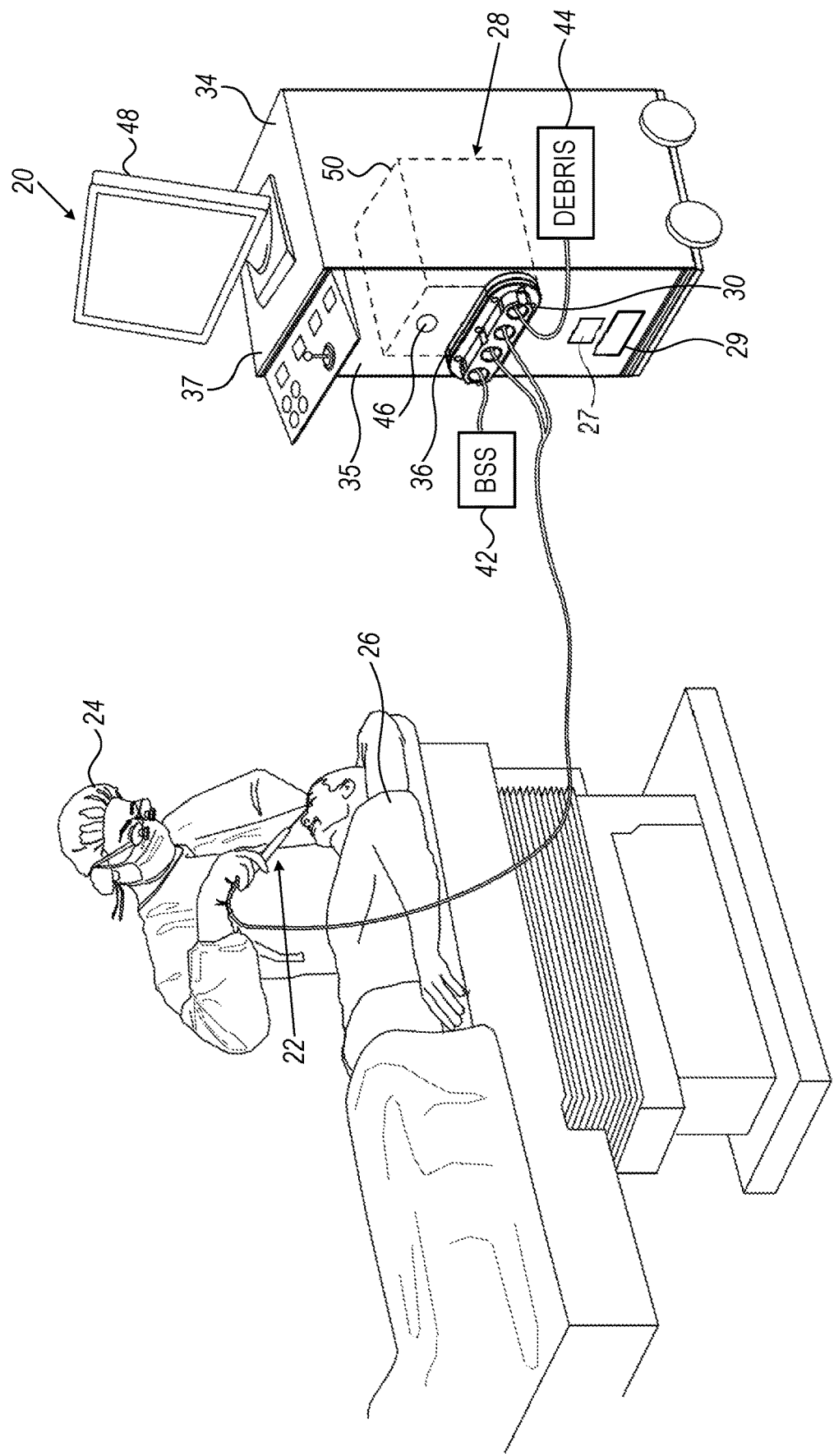
FIG. 1 is a schematic, pictorial illustration of a phacoemulsification system, in accordance with an embodiment of the present invention.

During a phacoemulsification procedure, irrigation and aspiration fluids are pumped in and out of the eye, respectively. One type of pump that may be particularly effective for this purpose is a progressive cavity pump, which comprises a rotor rotatably disposed inside a stator.

A phacoemulsification system may include a disposable cartridge comprising two progressive cavity pumps: one pump for pumping irrigation fluid to the eye, and another pump for pumping aspirating fluid from the eye. The disposable cartridge is inserted into a base which comprises a pair of motors and a mechanism for mechanically coupling the motors with the pumps. The advantage of such a system is that, following the phacoemulsification procedure, the relatively inexpensive cartridge may be discarded, while the base may be reused for the next procedure without necessarily requiring any prior cleaning. A disposable pump cartridge of this sort is described in U.S. patent application Ser. No. 17/318,665, filed May 12, 2021 and titled "Disposable Pump Cartridge," which is assigned to the assignee of the present patent application and whose disclosure is incorporated herein by reference.

The rotor of each pump is in constant moving contact with a stator, so that there is considerable friction in the system. The friction generates heat. If a progressive cavity pump loses its operating fluid, but continues pumping, it can easily damage itself; any extended operation with no fluid leads to irreversible damage.

Embodiments of the present invention that are described herein provide improved techniques for detecting and mitigating overheating of phacoemulsification irrigation and aspiration pumps. In some embodiments, sensors are disposed on inlet and outlet ports of a pump used in a phacoemulsification system where each sensor is configured to indicate fluid temperatures at a respective port. The sensors are also called hereinafter, "inlet sensor," and "outlet sensor." The inlet sensor and outlet sensor are coupled, respectively, with an inlet port and outlet port of the pump. The respective sensors are configured to sense the temperature of the fluid at the inlet and outlet ports.

A controller (or a processor) of the phacoemulsification system, or other standalone processing circuitry, is configured to detect a too high temperature of the pump in response to readings of the inlet sensor and the outlet sensor, and take a responsive action in response to the too high temperature. The controller is configured to detect the too high temperature of the pump by detecting a too high temperature difference between the inlet port and the outlet port. The responsive actions may comprise, for example, estimating pump temperature and/or alerting of pump heating and/or shutting down the pump. In the context of this disclosure the term "too high" means above a given threshold value or a temperature difference crossing a defined threshold.

The controller can be configured to compare a difference between the temperature of the fluid at the outlet port and the temperature of the fluid at the inlet port to a threshold, and to take a responsive action when the difference exceeds the threshold. Alternatively, or additionally, the controller may be configured to estimate an absolute temperature of the pump based on the readings of the inlet sensor and the outlet sensor, and to take a responsive action upon detecting a too high absolute temperature. In an embodiment, the threshold value may be set or programmed based on, inter alia, the type of pump used in the system.

In some embodiments the pump is part of a removably insertable cartridge. The sensors, such as infrared sensors, are integrated into the cartridge on inlet and outlet ports of the pump. Typically, the pump is one used as an irrigation pump and/or another pump used as an aspiration pump.

In another embodiment, the controller is configured to estimate excessive pump temperature by estimating differential temperatures of the pumped fluid. The controller then compares the estimated excessive pump temperature to a predefined limit on excessive pump temperature, and if the excessive pump temperature exceeds that limit, the controller shuts down the pump. Alternatively, the controller may estimate pump temperature and compare the estimated pump temperature to a predefined pump temperature limit.

The sensors are configured to monitor the temperature of the incoming and exiting fluid of each pump. Typically, while a pump is operating normally, there is a slight but constant temperature change of the fluid as it traverses the pump. However, if the friction increases in the pump, typically because of fluid flow reduction, the temperature change between the input and output of the pump increases. Using readings from the sensors, a processor monitors a temperature difference between temperatures of incoming and exiting fluid of each pump. If the processor detects an excessive increase in the temperature difference, it may stop pump operation and/or take any other suitable responsive action.

System Description

FIG. 1 is a schematic, pictorial illustration of a phacoemulsification system 20, in accordance with an embodiment of the present invention. System 20 comprises a phacoemulsification probe 22, with which a physician 24 may perform a phacoemulsification procedure on an eye of a patient 26. In particular, physician 24 may position the distal tip of probe 22 near or against the lens of the eye. Subsequently, the physician may cause an ultrasonic transducer in the probe to ultrasonically vibrate the distal tip of the probe to emulsify the lens.

System 20 further comprises a fluidics system 28. As the phacoemulsification procedure is performed, fluidics system 28 aspirates fluid and debris (e.g., pieces of the lens) from the eye while maintaining a flow of an irrigating fluid to the eye, such as a balanced salt solution (BSS), so as to maintain the intraocular pressure in the eye.

Figure 2:
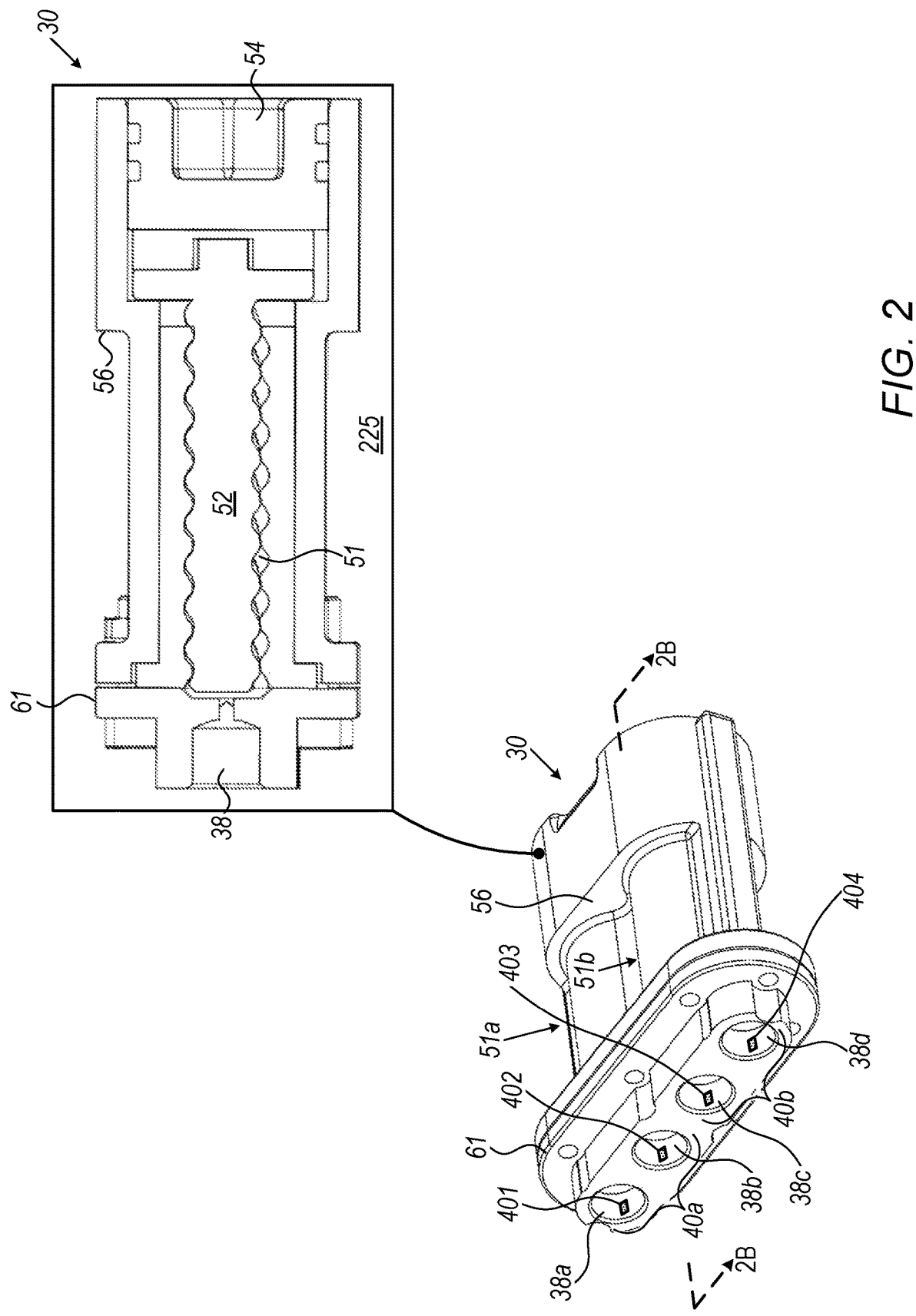
FIG. 2 schematically shows a disposable cartridge of pumps with infrared sensors for use with the phacoemulsification system of FIG. 1, in accordance with an embodiment of the present invention.

More specifically, fluidics system 28 comprises a disposable pump cartridge 30, further described in FIG. 2, comprising two positive displacement pumps, and a base 50 comprising two motors. A disposable pump cartridge similar to cartridge 30 is described in U.S. patent application Ser. No. 17/318,665, cited above.

Prior to the procedure, cartridge 30 is inserted into base 50 such that each pump is mechanically coupled with a different respective motor. Subsequently, one of the pumps, driven by one of the motors, pumps fluid from an irrigation reservoir 42 to the distal end of the probe 22. The other pump, driven by the other motor, pumps fluid and debris from the eye to a collection container 44.

Typically, base 50 is disposed within, or is an integrated part of, a console 34, and cartridge 30 is inserted into the base through a slot 36 in a side panel 35 or top panel 37 of console 34. Following the procedure, the cartridge is removed from the base, e.g., by pushing a button 46. Typically, the cartridge is then discarded, and another cartridge is used for the next procedure.

In the shown embodiment, a controller 27 of system 20 is configured to receive temperature-indicative readings from sensors integrated into cartridge 30, such as infrared sensors shown in FIG. 2. The sensors indicate pump temperatures by measuring irrigation and aspiration fluid temperatures. In an embodiment, the sensors are disposed on inlet and outlet ports of an irrigation pump and of an aspiration pump of removable insertable cartridge 30. Controller 27 is further configured to take a responsive action based a difference between the inlet temperature and the outlet temperature crossing a defined threshold. The controller may, depending on sensor readings, warn of pump heating and/or shut down system 20 to protect the pumps from damage, and, in rare cases, from potential hazard to the patient eye, if fluidics system 28 fails during the procedure.

System 20 further comprises a processor 29 and/or other circuitry (not shown) configured to drive the ultrasonic transducer in probe 22, control fluidics system 28, display relevant information on a display 48, and/or perform any other relevant function.

In another embodiment, processor 29 is configured to receive the temperature-indicative readings from the sensors integrated into cartridge 30. In this embodiment, the processor may, depending on sensor readings, warn of pump heating and/or shut down system 20 to protect the pumps from damage, and, in rare cases, from potential hazard to the patient eye, if fluidics system 28 fails during the procedure.

In some embodiments, controller 27 includes processing capability and/or receives input from processor 29.

Cartridge with Infrared Temperature Sensors on Fluid Inlet and Outlet

A more detailed description of cartridge 30 is hereby provided with reference to FIG. 2, which shows disposable cartridge 30 having pumps with infrared sensors (401, 402, 403, 404) for use with phacoemulsification system 20 of FIG. 1, in accordance with an embodiment of the present invention.

Cartridge 30 is shaped to define two stators (51), irrigation pump stator 51a and aspiration pump stator 51b, and respective pairs of irrigation ports 38a and 38b, and aspiration ports 38c and 38d, in fluidic communication with stators 51a and 51b, respectively. Ports 38a-d may be disposed, for example, at the front of the cartridge.

Stators 51a and 51b may be metallic or polymeric. Cartridge 30 further comprises two rotors rotatably disposed, respectively, within the stators. The rotors may be metallic or polymeric. As inset 225 shows, the cartridge further comprises two respective rotors 52 rotatably disposed, respectively, within the stators. (The cross section in inset 225 is taken through one of the stators along 2B, so as to reveal the rotor 52 disposed therein.) Rotors 52 may be metallic or polymeric.

As described above with reference to FIG. 1, typically one pair 40a of ports 38a and 38b of cartridge 30 is connected to irrigation reservoir 42 and to the probe 22, while the other pair 40b of ports 38c and 38d is connected to the probe 22 and to collection container 44. Thus, rotation of the rotors within the stators (i) causes fluid to flow from reservoir 42, through pair 40a, to the distal tip of probe 22, and (ii) causes fluid and debris to flow from the eye, through pair 40b, to collection container 44.

In some embodiments, cartridge 30 comprises a front panel 61, which, by virtue of being fastened to the remainder of the cartridge (e.g., via screws), stabilizes stators 51a and 51b and prevents leakage from the cartridge. Front panel 61 may be grasped when inserting the cartridge into, or removing the cartridge from, the base 50. Alternatively, or additionally, cartridge 30 may comprise a handle (not shown), which may be grasped when inserting or removing the cartridge.

Sensors 401 and 402 measure irrigation fluid temperatures at the inlet and outlet of the irrigation pump, respectively. Sensors 403 and 404 measure aspiration fluid temperatures at the inlet and outlet of the aspiration pump, respectively. Therefore, sensor pairs 401, 402 and 403, 404 can provide an estimation of how much the pumps operation heats the pumped fluids, and from this indication controller 27 can provide an indication of the heat of the pumps. In the embodiments described herein, sensors 401-404 are infrared sensors. Alternatively, however, any other suitable type of sensor capable of measuring fluid temperature can be used.

In particular, if the controller 27 deems that the estimated temperature of at least one of the irrigation and aspiration pumps deviates from predefined limits, and in particular exceeds a given allowable pump temperature or allowable threshold level of pump heating, controller 27 turns off the pumps and alerts the physician.

Figure 3:
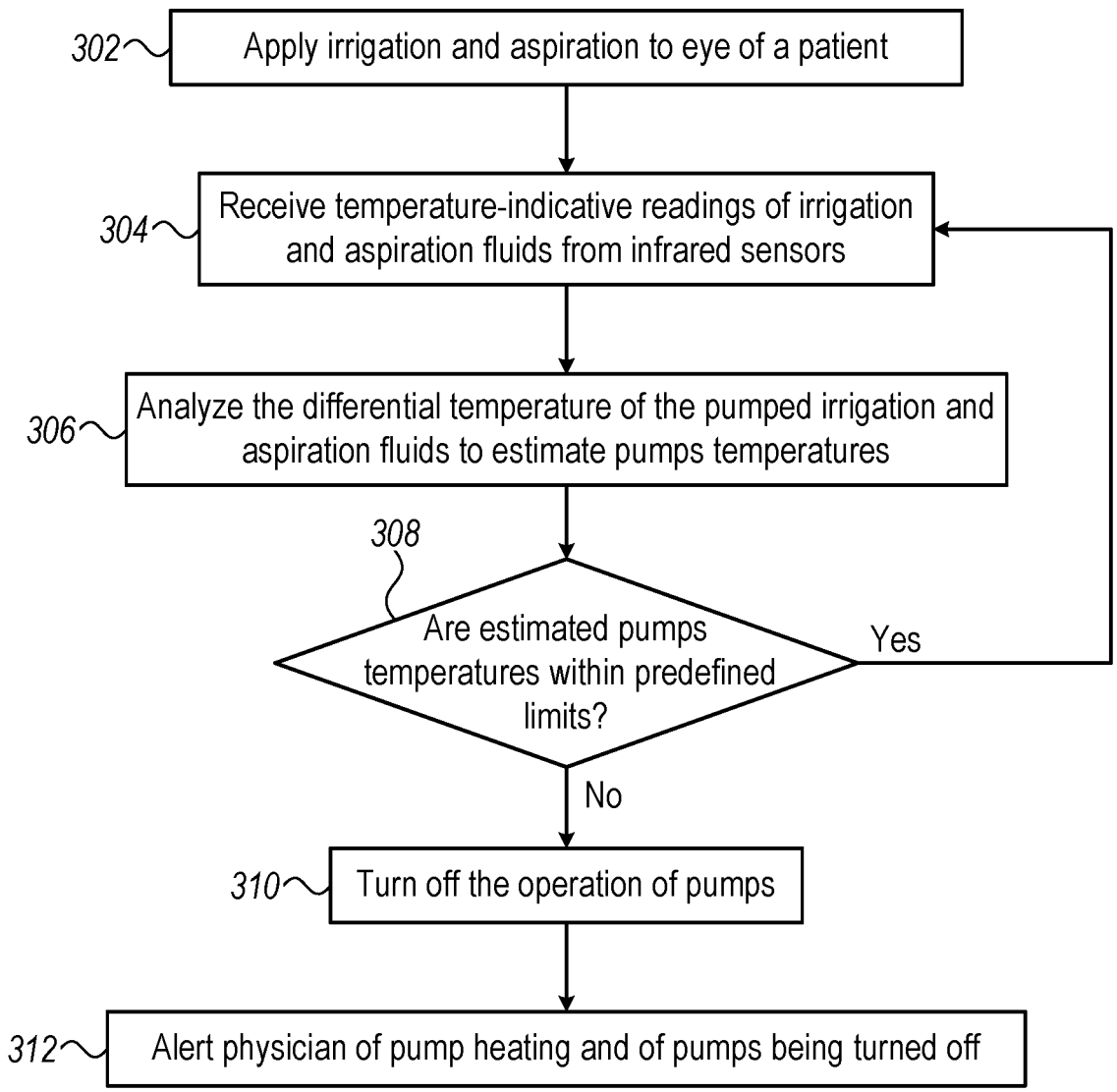
FIG. 3 is a flow chart of a method for monitoring fluid temperature using the infrared sensors of the cartridge of pumps of FIG. 2, in accordance with other embodiments of the present invention.

FIG. 3 is a flow chart of a method for monitoring fluid temperature using the infrared sensors (401, 402, 403, 404) of cartridge 30 of the pumps of FIG. 2, in accordance with other embodiments of the present invention. The process begins with applying irrigation and aspiration to an eye of a patient during a phacoemulsification procedure, at irrigation and aspiration step 302.

During operation, controller 27 receives temperature-indicative readings from infrared sensors (401, 402, 403, 404), of irrigation and aspiration fluids, at reading receiving step 304.

The controller analyzes the differential temperature of the pumped irrigation and aspiration fluids to estimate pump temperatures, at pump temperature estimation step 306.

At step 308, if the estimated temperatures are within predefined limits, and in particular below a given allowable pump temperature or level of pump heating threshold, the controller continues the operation of the pumps, by returning to step 302. On the other hand, if one or more of the estimated temperatures deviate from predefined limits, and in particular exceeds a predefined allowable pump temperature or level of pump heating threshold, the controller turns off the operation of the pump(s), at step 310.

The controller alerts the physician of pump heating and/or of the pumps being turned off, at an alerting step 312.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A phacoemulsification system, comprising:
    an irrigation pump and an aspiration pump, each of the irrigation pump and the aspiration pump configured to pump a fluid in a fluidics system of the phacoemulsification system, wherein the irrigation pump and the aspiration pump are configured to maintain an intraocular pressure within an eye of a patient;
    an inlet sensor, which is positioned within an inlet port of a surgical cartridge of the fluidics system and is configured to sense a first temperature of the fluid passing through the inlet port, wherein the surgical cartridge comprises at least a portion of one of the irrigation pump or the aspiration pump;
    an outlet sensor, which is positioned within an outlet port of the surgical cartridge and is configured to sense a second temperature of the fluid passing through the outlet port; and
    a controller coupled with the irrigation pump and the aspiration pump, wherein the controller is configured to:
        calculate a difference in a temperature of the fluid between the first temperature of the fluid and the second temperature of the fluid,
        estimate, based on the difference in the temperature of the fluid calculated, an estimated temperature of at least one of the irrigation pump or the aspiration pump, and take a responsive action to control at least one of the irrigation pump or the aspiration pump when the estimated temperature crosses a defined threshold.

2. The phacoemulsification system according to claim 1, wherein the responsive action is taken when the estimated temperature exceeds the defined threshold.

3. The phacoemulsification system according to claim 1, wherein the estimated temperature is controller is configured to estimate an absolute temperature of the one of the irrigation pump or aspiration pump based on the readings of the inlet sensor and the outlet sensor, and to take the responsive action upon detecting a too high absolute temperature.

4. The phacoemulsification system according to claim 1, wherein the responsive action comprises shutting down at least one of the irrigation pump or the aspiration pump.

5. The phacoemulsification system according to claim 1, wherein the inlet sensor and the outlet sensor are infrared sensors.

6. The phacoemulsification system according to claim 1, wherein at least one of the irrigation pump or the aspiration pump is a progressive cavity pump.

7. The phacoemulsification system according to claim 1, wherein the surgical cartridge is irrigation pump, the aspiration pump, the inlet sensor and the outlet sensor are part of a removably insertable cartridge for use in the phacoemulsification system.

8. The phacoemulsification system according to claim 1, wherein the controller is implemented utilizing processing circuitry.

9. A method implemented in a phacoemulsification system, the method comprising:
sensing, with an inlet sensor positioned within an inlet port of a surgical cartridge, a first temperature of a fluid passing through the inlet port in a fluidics system of the phacoemulsification system; wherein the surgical cartridge comprises at least a portion of one of an irrigation pump or an aspiration pump; and wherein the irrigation pump and the aspiration pump are configured to maintain an intraocular pressure within an eye of a patient;
sensing, with an outlet sensor positioned within an outlet port of the surgical cartridge, a second temperature of the fluid passing through the outlet port;
calculating a difference in a temperature of the fluid between the first temperature of the fluid and the second temperature of the fluid,
estimating, based on the difference in the temperature of the fluid calculated, an estimated temperature of at least one of the irrigation pump or the aspiration pump; and
taking a responsive action to control at least one of the irrigation pump or the aspiration pump when the estimated temperature crosses a defined threshold.

10. The method according to claim 9, wherein the inlet sensor and the outlet sensor are infrared sensors.

11. The method according to claim 9, wherein the surgical cartridge is a removably insertable cartridge for use in the phacoemulsification system.

12. The method according to claim 9, wherein the responsive action is taken when the estimated temperature exceeds the defined threshold.

13. The method according to claim 9, wherein the estimated temperature is an absolute temperature.

14. The method according to claim 9, wherein the responsive action comprises shutting down at least one of the irrigation pump or the aspiration pump.

15. The method according to claim 9, wherein at least one of the irrigation pump or the aspiration pump is a progressive cavity pump.

* * * * *